United States Patent
Ni et al.

(10) Patent No.: US 10,576,038 B2
(45) Date of Patent: Mar. 3, 2020

(54) METHOD FOR PREPARATION OF REDUCIBLE DEGRADABLE HYPERBRANCHED POLYMERIC MICELLES

(71) Applicant: JIANGNAN UNIVERSITY, Wuxi, Jiangsu (CN)

(72) Inventors: Caihua Ni, Jiangsu (CN); Yamin Zhou, Jiangsu (CN); Liping Zhang, Guangdong (CN); Gang Shi, Jiangsu (CN)

(73) Assignee: JIANGNAN UNIVERSITY, Wuxi, Jiangsu (CN)

( * ) Notice: Subject to any disclaimer, the term of this patent is extended or adjusted under 35 U.S.C. 154(b) by 28 days.

(21) Appl. No.: 15/780,320

(22) PCT Filed: Jul. 29, 2016

(86) PCT No.: PCT/CN2016/092187
§ 371 (c)(1),
(2) Date: May 31, 2018

(87) PCT Pub. No.: WO2017/107486
PCT Pub. Date: Jun. 29, 2017

(65) Prior Publication Data
US 2018/0360753 A1    Dec. 20, 2018

(30) Foreign Application Priority Data

Dec. 21, 2015    (CN) ............................ 2015 1 0971607

(51) Int. Cl.
*A61K 9/107* (2006.01)
*C08G 83/00* (2006.01)
(Continued)

(52) U.S. Cl.
CPC ............ *A61K 9/1075* (2013.01); *A61K 47/34* (2013.01); *B01J 13/04* (2013.01); *B01J 13/16* (2013.01);
(Continued)

(58) Field of Classification Search
CPC ........................... A61K 9/1075; C08G 83/005
See application file for complete search history.

(56) References Cited

FOREIGN PATENT DOCUMENTS

CN        105395483 A    *    3/2016

OTHER PUBLICATIONS

CN105395483A; English Machine Translation, provided by Google pateents on Aug. 5, 2019 (Year: 2016).*

(Continued)

*Primary Examiner* — Timothy P Thomas
(74) *Attorney, Agent, or Firm* — Enshan Hong; VLP Law Group LLP

(57) ABSTRACT

Provided are a reducible degradable hyperbranched-polymer nanomicelle and a method for preparation thereof and an application thereof. Cystamine and polyethylene glycol diglycidyl ether are polymerized by means of a nucleophilic addition mechanism; in one step, a hyperbranched polymer alternatingly arising from cystamine and polyethylene glycol structural units is synthesized and obtained; then, a hyperbranched nanomicelle is formed by means of self-assembly during the process of dialysis. The hyperbranched-polymer chain segments contain both tertiary aminos and disulfide bond structural units and have pH- and reduction responsiveness, and the hyperbranched three-dimensional cavity structure imparts a drug-carrying ability to the nanomicelle.

7 Claims, 5 Drawing Sheets

(51) Int. Cl.
*A61K 47/34* (2017.01)
*B01J 13/04* (2006.01)
*B01J 13/16* (2006.01)

(52) U.S. Cl.
CPC .......... *C08G 83/00* (2013.01); *C08G 83/005* (2013.01); *C08G 83/006* (2013.01)

(56) References Cited

OTHER PUBLICATIONS

Hamid et al.; "Epoxy-amine synthesized hydrogel scaffolds for soft-tissue engineering"; 2010; Biomaterials; 31: 6454-6467 (Year: 2010).*
Ozcelik et al.; "Ultrathin chitosan-poly(ethylene glycol) hydrogel films for corneal tissue engineering"; 2013; Acta Biomaterialia; 9: 6594-6605 (Year: 2013).*

* cited by examiner

METHOD FOR PREPARATION OF REDUCIBLE DEGRADABLE HYPERBRANCHED POLYMERIC MICELLES

RELATED APPLICATIONS

This is a U.S. national stage of international application No. PCT/CN2016/092187 filed on Jul. 29, 2016, which claims priority from China Patent Application No. 201510971607.9 filed on Dec. 21, 2015, the entire content of which is incorporated herein as reference.

TECHNICAL FIELD

The invention relates to the technical field of biomedical materials, in particular to a reducible degradable hyperbranched polymeric micelles and the preparation method thereof.

BACKGROUND OF THE INVENTION

Nano drug carriers can achieve the passive targeting to the tumor tissues by the high permeability and retention (EPR) effect on tumor tissues, which greatly improves the drug utilization and reduces the toxicity and side effects of the free drugs on the normal tissues. Polymeric micelles, as drug carriers, have the advantages of solubilizing hydrophobic drugs, improving drug stability and sustained-release drugs.

In order to achieve the goal of targeting drug release to the tumor tissue, there are many reports on biodegradable carriers with environmental intelligent responsiveness (such as pH, reduction potential, enzyme and so on). In recent years, some researchers focus on environmental intelligent responsive hyperbranched polymers. It is found that the hyperbranched polymers have novel structures and unique properties such as high solubility, low viscosity, three-dimensional interior cavity spherical structures and so on. A large number of cavities in the structure can be used for hydrophobic drug loading. The drug loading is improved during the process. Hyperbranched polymers can be degraded into non-toxic small molecules and release drugs by acidic or reductive stimulations of the tumor cell environment.

However, in literatures the reported synthetic methods for preparation of environmental responsive hyperbranched polymers usually take many steps, and a lot of organic solvents are needed in the preparations, which limits the applications in biomedical fields. At the same time, most of the hyperbranched polymer micelles currently reported do not exhibit reductive responsiveness and are inevitably retained in vivo.

SUMMARY OF THE INVENTION

In order to solve the above technical problems, the aim of the present invention is to provide a method for preparation of hyperbranched polymer nano micelles by one step in the water phase. The prepared hyperbranched polymer nano micelles are biodegradable under reducible conditions of the body, and they have a good biocompatibility for application as biomedical materials.

In addition, the invention discloses a reducible degradation hyperbranched polymer nano micelle that has a multi core-shell structure consisting of polyethylene glycol and disulfur bonds chains alternately. In order to make the amino groups to distribute in peripheral of the hyperbranched polymer, the molar number of the reactant cystamine is adjusted to two times of the molar number of the polyethylene glycol diglycidyl ether, in order to guarantee the excess of the amino group. The hyperbranched structure and the alternating chains of polyethylene glycol with disulfur bonds in the polymers have their respective functional effects: (1) The hyperbranched three-dimensional cavity structure can effectively improve the loading rate for hydrophobic drugs; (2) The polyethylene glycol segment has excellent biocompatibility, flexibility and hydrophilicity, and can be used as hydrophilic segments in the multi core-shell structure; (3) The cystamine structural units are hydrophobic segments of the multi core-shell structure, and they are useful to encapsulate hydrophobic drugs; (4) The disulfur bond is stable in normal cells and non reducing environments, but it breaks down in the reducing environment of the tumor, so that the nano micelle has a good reducibility.

In the invention, polyethylene glycol diglycidyl ether is used. In order to balance the hydrophilicity and micellability of the hyperbranched polymer effectively, the molecular weight of polyethylene glycol diglycidyl ether is 218~482 in the reaction.

The invention also provides a preparation method for reducible degradation hyperbranched polymeric micelles, which comprises the following steps:

1) Cystamine is obtained by the neutralization reaction of cystamine dihydrochloride and alkali.

2) Hyperbranched polymer is obtained by nucleophilic addition reaction of cystamine and polyethylene glycol diglycidyl ether.

3) The nano micelles are obtained through dialysis of the hyperbranched polymer obtained in step 2).

Specifically, in step 1), the alkali is one or several of the following compounds: sodium hydroxide, potassium hydroxide, sodium carbonate, sodium bicarbonate, tetraethylammonium hydroxide and triethylamine.

Specifically, sodium hydroxide solution is used to neutralize cystamine dihydrochloride, and the reaction condition is in an ice bath.

More specifically, in step 1), an exaction is involved and the mixed solvents of ether and tetrahydrofuran are used to extract cystamine.

Further, in step 2), polyethylene glycol diglycidyl ether with number average molecular weight of 218~482 is used, in order to balance the hydrophilicity and micellability of the hyperbranched polymer effectively. The optimization molecular weight of polyethylene glycol diglycidyl ether is 350.

Also, in step 2), the molar ratio of cystamine to polyethylene glycol diglycidyl ether can be set in a range of 0.5~3:1, the optimization is 2~3:1, Cysteamine excess can produce a hyperbranched polymer with amino groups in peripheral.

In some specific embodiments, the molar ratios of cystamine and polyethylene glycol diglycidyl ether are 3: 1, 2: 1, 2: 2 or 2: 3, preferably 3:1 or 2:1.

Further, in step 2), the nucleophilic addition temperature is 60-70° C., preferably 60-65° C.

Further, the nucleophilic addition reaction time is 20-30 h. Preferably, the nucleophilic addition reaction is carried out in a 60° C. oil bath pan for 24 h.

Further, in step 2), the solvent is one or several of the following materials: water, N,N-dimethyl formamide, formamide, tetrahydrofuran, 1,4-dioxane and dimethyl sulfoxide.

Preferably, the water is deionized water or distilled water.

Further, in step 3), the hyperbranched polymers are dialyzed using a dialysis bag with cut-off molecular weight of 3500~7000, the dialysis time is 48~72 hours. The purpose of the dialysis is to remove the unreacted small molecules and oligomers, because the polymers with low molecular weight are not easy to form micelles, and the dialysis bags have various specifications. The choice of dialysis bags with a molecular weight of more than 3500 is suitable.

Further, the solvent used for dialysis is water, preferably ultrapure water, deionized water or distilled water.

It is preferable to dialyze the hyperbranched polymers in ultrapure water no less than 48 hours by using a dialysis bag with cutoff molecular weight of 3500.

Cystamine contains two terminated amino groups, while polyethylene glycol diglycidyl ether contains two terminated epoxy groups, and a typical nucleophilic addition reaction can take place between the amino group and the epoxy group. When the molar number of amino groups involved in reaction is greatly more than that of epoxy groups, hyperbranched polymers with amino terminated ends can be obtained. Therefore, the number of cystamine is two times more than the number of polyethylene glycol diglycidyl ether when designing the synthetic formula.

The invention also discloses an application of reducible degradable hyperbranched polymeric micelles for the preparation of chemotherapeutic drug carrier. Glutathione is a reductive three peptide containing a sulfhydryl group. Its concentration in tumor cells is 100~1000 times higher than that in body fluids and normal cells. Under the reduction stimulation of glutathione, disulfide bonds in the hyperbranched polymer are rapidly broken and the polymer degrades and releases the loaded drugs. At the same time, the tumor cells are weak acidic environment. The nano micelles contain a large number of primary amino, secondary amino and tertiary amino groups, so the nano micelles have pH sensitivity. Under the acidic stimulation of tumor cells, the structure of micelles is changed, which leads to drug release.

With the above scheme, the invention has at least the following advantages:

(1). Due to the presence of structural units such as primary amino, secondary amino and tertiary amino groups and disulfur bonds, the hyperbranched polymers have pH and reductive responsiveness. In the weak acid and reductive environment of the tumor cells, the nano micellar structure is destroyed and the drug is released to the tumor site.

(2). The disulfur bond is located in the skeleton of the hyperbranched polymer. After the micelle enters into tumor cells, the disulfur bond breaks under the condition of high concentration of glutathione in the cell, which makes the micelle completely degraded into small molecules in the body, and the small molecules can be easily removed from the kidney. Therefore, the nano micelle has a practical application value as an anticancer drug carrier.

(3). The nano micelles are cytotoxic and meet the safety standards for human use.

(4). The synthetic method is simple under mild conditions without employing any catalysts and poisonous organic solvents. The product is pure without by-products and impurities.

(5). The unique three-dimensional cavity structure of hyperbranched polymers is beneficial to increase the drug loading.

DESCRIPTION OF PREFERRED EMBODIMENTS

The detailed implementation of the invention is further described as follows. The following embodiments are used to illustrate the invention, but not to limit the scope of the invention.

EXAMPLE 1

(1) Preparation of Cystamine

Accurately weighed 12.15 g powdered cystamine dihydrochloride is dissolved in 16 mL deionized water, then 60 mL ether and 24 mL tetrahydrofuran are added under stirring. In the ice bath, 40% NaOH solution (66.7 mL) is added dropwise into the mixture above under magnetic stirring for one hour; the upper organic phase is separated. The lower aqueous phase is extracted with a mixture of 50 mL ether and 18 mL tetrahydrofuran. The organic phase is combined and dried with 4 g NaOH for two hours, after filtration the volatile ether and tetrahydrofuran are removed through evaporation, and finally 6.2 g cystamine is obtained with a yield of 75.5%.

Figure 1:
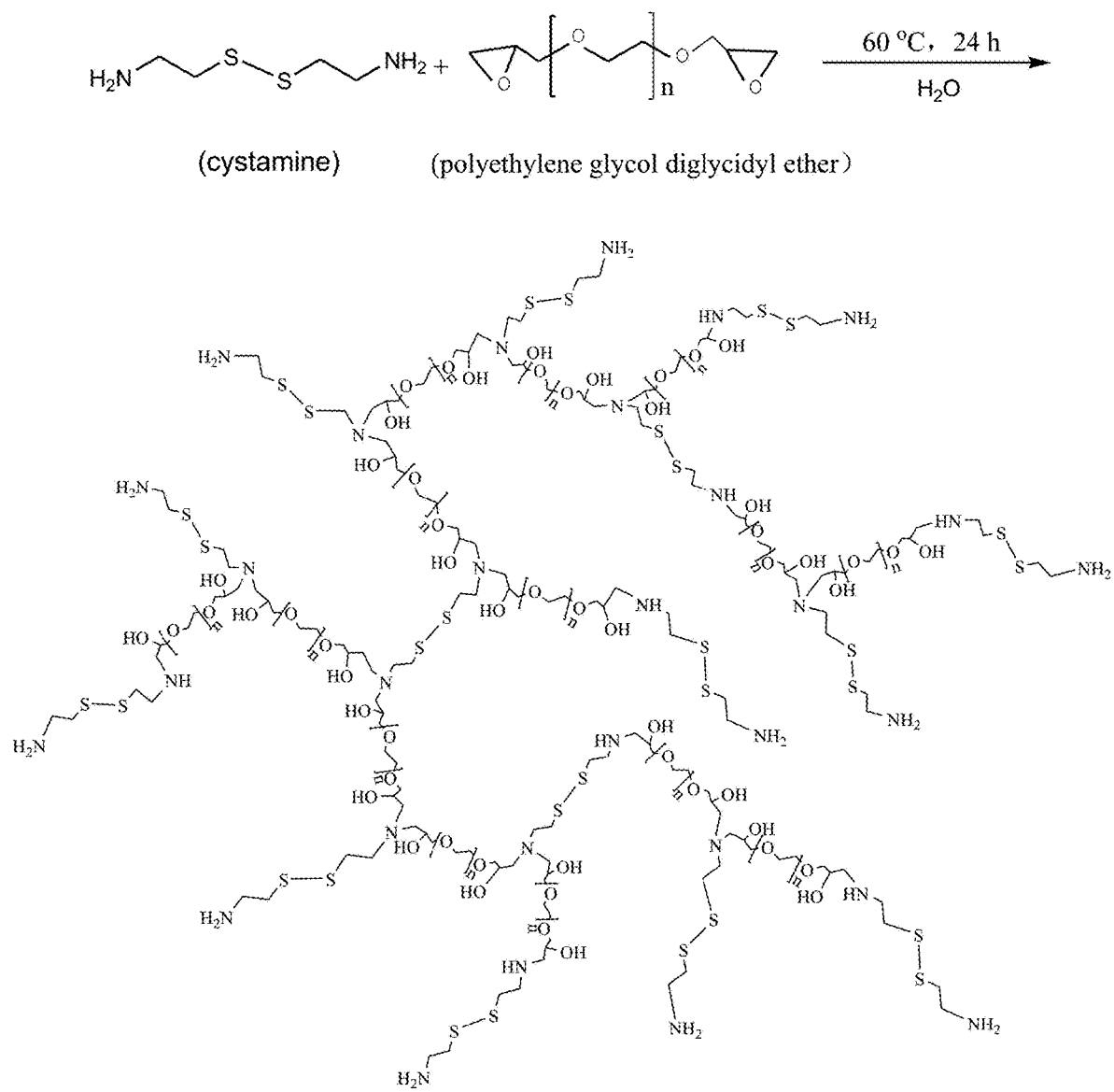
FIG. 1 is a schematic diagram of the reaction between cystamine and polyethylene glycol diglycidyl ether in the invention.

(2) Preparation of Hyperbranched Polymers:

Cystamine 304 mg is dissolved into 8 mL ultrapure water under magnetic stirring till completely dissolved, and polyethylene glycol diglycidyl ether 350 mg with 8 mL of ultrapure water is added into the above solution, the reaction is carried out at 60° C. for 24 hours, the hyperbranched polymer solution CP21 is obtained. The synthesis route of cystamine and polyethylene glycol diglycidyl ether is shown in FIG. 1.

Four kinds of hyperbranched polymers CP31, CP21, CP22 and CP23 with different molar ratios of cystamine to polyethylene glycol diglycidyl ether are provided in Table 1.

TABLE 1

A list of synthetic formulas for hyperbranched polymers

| Sample ID | Cystamine (Number average molecular weight 152) | polyethylene glycol diglycidyl ether (Number average molecular weight 350) |
|---|---|---|
| CP31 | 3 (mmol) | 1 (mmol) |
|      | 456 (mg) | 350 (mg) |
| CP21 | 2 (mmol) | 1 (mmol) |
|      | 304 (mg) | 350 (mg) |
| CP22 | 2 (mmol) | 2 (mmol) |
|      | 304 (mg) | 700 (mg) |
| CP23 | 2 (mmol) | 3 (mmol) |
|      | 304 (mg) | 1050 (mg) |

Figure 2:
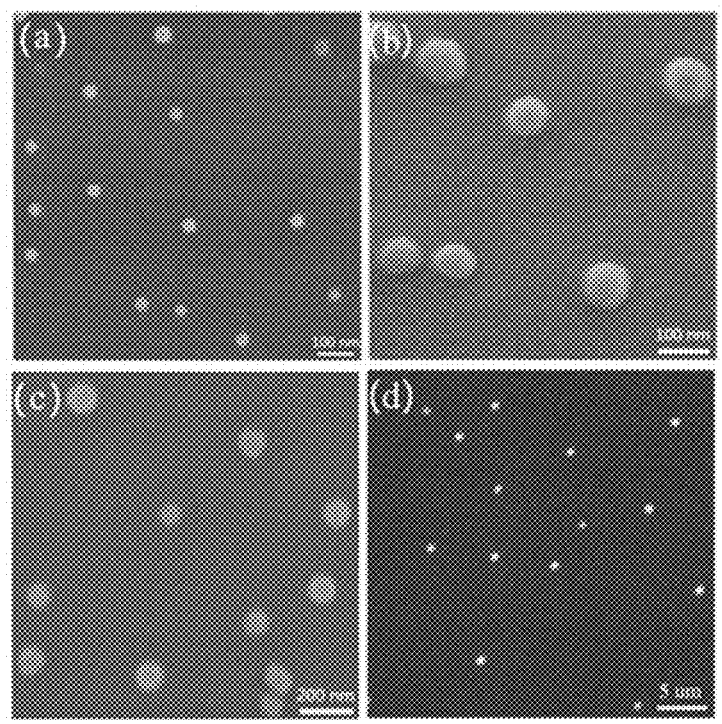
FIG. 2 are SEM images of the reducible degradable hyperbranched polymeric micelles in the invention; a, b, c and d represent the molar ratio of cystamine to polyethylene glycol diglycidyl ether is 3:1, 2:1, 2:2 or 2:3 respectively in the preparations.

(3) Preparation of Reducible Degradable Hyperbranched Polymeric Nano Micelles:

The polymer solution obtained in step 2) is poured into a dialysis bag (with a cutoff molecular weight 3500), dialysing 3 days in ultrapure water, and the dialysate is changed every 4 hours, and finally the hyperbranched polymeric nano micelles are obtained. The cutoff molecular weight of dialysis bags can be selected according to the specific use process, usually not less than 3500. The scanning electron microscopy (SEM) photographs of the reducible degradable hyperbranched polymeric micelles are showed in FIG. 2, from a to d, respectively, corresponding to the polymers of CP31, CP21, CP22 and CP23 in Table 1. Obviously, the micelle morphologies are basically spherical, and the particle size distributions are relatively uniform.

The reducible and degradable hyperbranched polymer dry powder can be prepared through freeze drying of the nano micelles solution.

According to the application requirements for the nano particle sizes, nano micelles with different particle sizes can be obtained by controlling the mole ratio of cystamine and polyethylene glycol two glycidyl ether. The nano micelle sample with the molar ratio of cystamine to polyethylene glycol diglycidyl ether at 2:1 has regular sphericity and suitable for applications, and the chemical properties of nano micelles with different particle sizes are same, therefore, it is taken as a representative for the subsequent implementation case unless otherwise stated.

Figure 3:
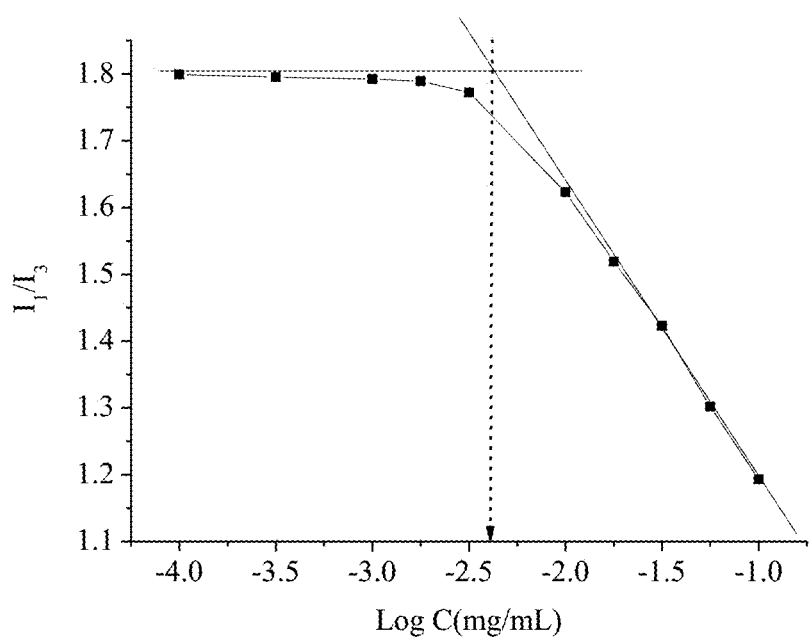
FIG. 3 shows the critical micelle concentration (mg/mL) of the reducible degradable hyperbranched polymeric micelles with a molar ratio of cystamine to polyethylene glycol diglycidyl ether at 2:1 in pH 7.4. Abscissa C is the concentration of polymer micelles.

Measurement of Critical Micelle Concentration of the Reducible Degradable Hyperbranched Polymeric Micelles Solution of reducible degradable hyperbranched polymeric micelles CP21 with a particular concentration are prepared. Then, 30 μL of pyrene acetone solution with concentration of $1.622 \times 10^{-5}$ g/mL is added to 4 mL of the hyperbranched polymeric micelles solution. The solution is oscillated several times till to uniform. After evaporation of acetone the emission spectrum is determined by the fluorescence spectrophotometer, the excitation wavelength is set to 330 nm, the width of the excitation and emission of the slit is 5 nm, and the scanning range is 350~500 nm. A curve is drawn by taking the logarithm micelle concentration as X axis and $I_1/I_3$ as Y axis. As can be seen from FIG. 3, the critical micelle concentration of the micelle CP21 is very low, only 3.98 mg/L, so it has strong anti-dilution ability.

The Reduction Sensitivity of the Reducible Degradable Hyperbranched Polymeric Micelles The reducible degradable hyperbranched polymeric micelles CP21 prepared in Example 1 are placed in a glutathione solution with concentration of 10 mmol/L, in the micelles cysteamine: polyethylene glycol diglycidyl ether is 2:1, the particle size change of the micelles at different time is recorded by laser light scattering for observing reduction sensitivity of the micelles.

Figure 4:
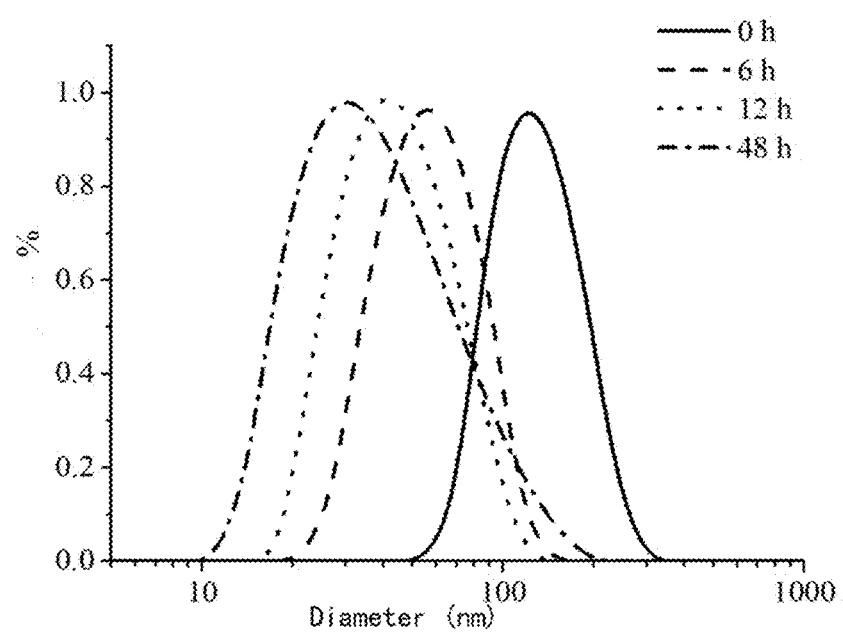
FIG. 4 shows the particle size changes of the reducible degradable hyperbranched polymeric micelles in 10 mM glutathione solution at different time. The molar ratio of cystamine to polyethylene glycol diglycidyl ether is 2:1 in the sample.

The results are showed in FIG. 4. The particle size becomes smaller after 6 hours contacting with 10 mmol/L glutathione (GSH) solution, indicating that most of the disulfur bonds break and the micelle structure is destroyed.

Figure 5:
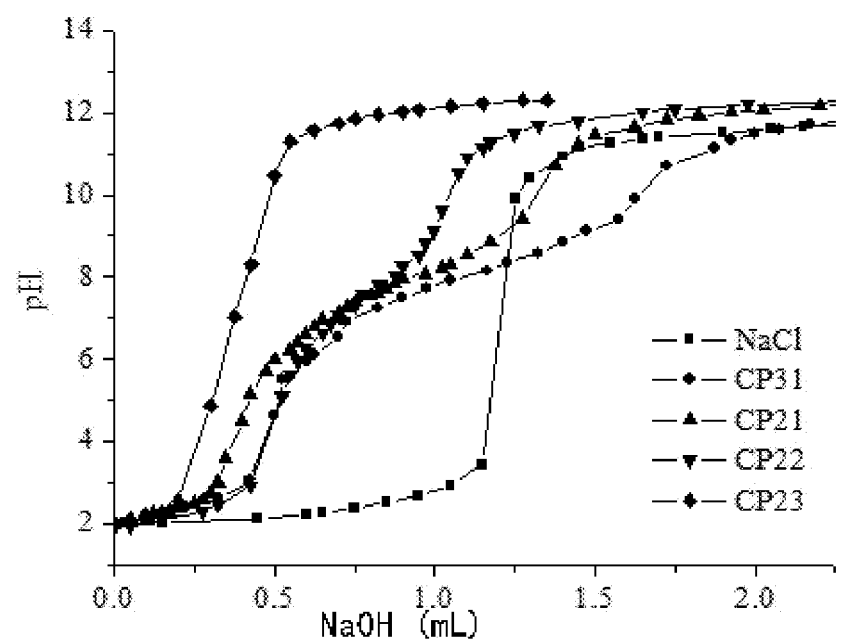
FIG. 5 shows acid-base titration curves for the reducible degradable hyperbranched polymeric micelles in the present invention.

The pH Sensitivity of the Reducible Degradable Hyperbranched Polymeric Micelles (1). The 50 mg dry powder of the reducible degradable hyperbranched polymeric micelles CP21 prepared in Example 1 is dissolved in 5 mL of 150 mmol/L NaCl solution, the pH of the solution is adjusted to pH 2 by 1.0 mol/L HCl solution, and is titrated with 0.1 mol/L NaOH solution. In the titration study 5 mL of 150 mmol/L NaCl solution is used as a control group. As shown in FIG. 5, the NaCl solution has no buffering platform, so it has almost no pH buffering capacity. However, the titration curves for the hyperbranched polymeric micelles solutions decline slowly in the pH range of 7.4~5, and with the increase of cystamine content, the curve slope is more gentle, the buffer capacity is obviously improved. Therefore, the reducible degradable hyperbranched polymeric micelles have good pH sensitivity.

Figure 6:
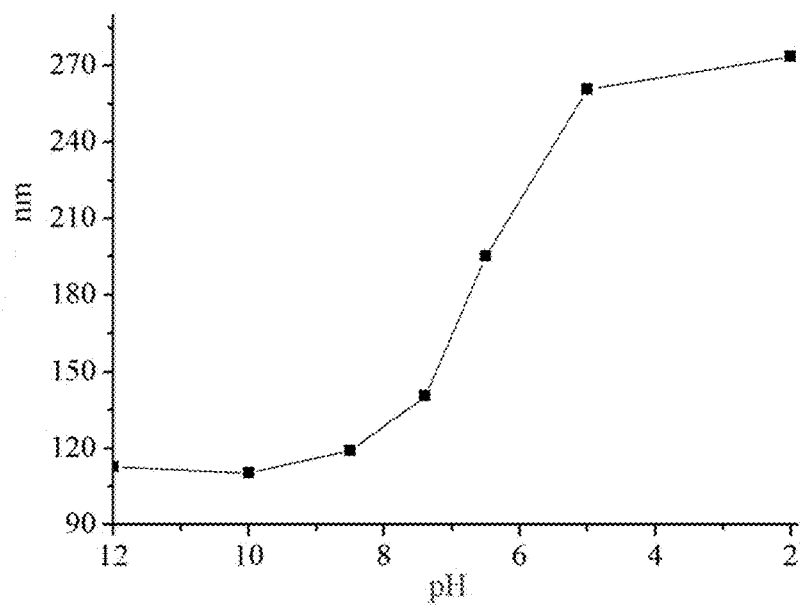
FIG. 6 shows the diameter changes of nano micelles with pH in the solutions. The molar ratio of cystamine to polyethylene glycol diglycidyl ether is 2:1 in the sample.

(2). Taking the reducible degradation of hyperbranched polymer CP21 prepared in Example 1 as an example. The pH value of the aqueous solution is controlled in the range of 2~12 by adding 0.1 mol/L HCl(aq) or 0.1 mol/L NaOH (aq) solution. The particle sizes and the distributions are determined by DLS. FIG. 6 shows that the particle size changed little under the conditions of extremely alkaline and extremely acidic; but the particle size of the micelles increases from 119 nm to 260.7 nm when the pH changes from neutral pH=7.4 to the lysosomal environment pH=5.0, because the tertiary amino, secondary amino and primary amino groups in the polymer skeleton structure will adsorb protons in large quantities, the hyperbranched polymer is highly positively charged, the internal electrostatic repulsion causes the volume expansion of the particles.

Biocompatibility of the Reducible Degradable Hyperbranched Polymeric Micelles

Taking the reducible degradation of hyperbranched polymer CP21 prepared in Example 1 as an example. The micelle sample CP21 is taken as an example. The RPMI-1640 medium containing 10% fetal bovine serum is employed for incubation. 3T3 and Hela cells are planted on the 96 pore plate ($1 \times 10^4$ cells/mL). After incubation at 37° C. for 24 h, the culture solution was abandoned. The micelle solution 100 μL with different concentration is added in to the hole, each group contains 6 holes. After incubation at 37° C. for 24 h, the culture solution was abandoned. Then, 20 μL MTT solution is added to the hole for additional 4 hours incubation, and the culture solution was abandoned. 150 μL DMSO is added to each hole under shaking, the absorbance of the solution is determined by enzyme meter at 570 nm, and the cell viability (%) is calculated.

Figure 7:
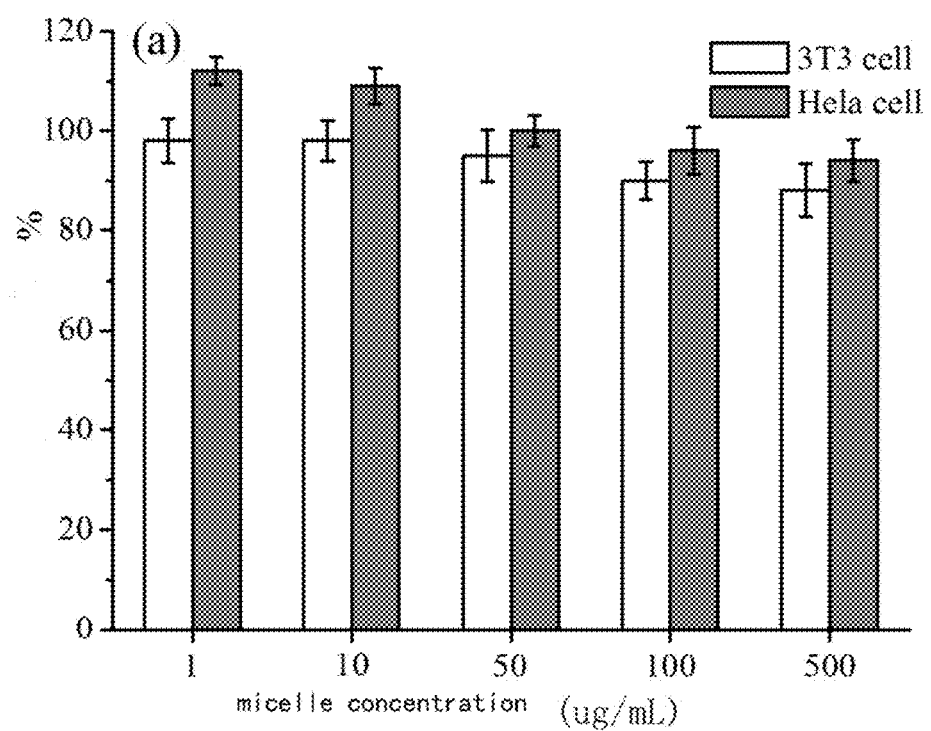
FIG. 7 shows the cytotoxic column result of the reducible degradable hyperbranched polymeric micelles: The molar ratio of cystamine to polyethylene glycol diglycidyl ether is 2:1 in the sample.

As shown in FIG. 7, cell viability (%) of 3T3 and Hela cells in different concentrations of the micelle solutions are in the range of 92%~110%. The cell viabilities of the two kinds of cells are relatively close under the same conditions.

The cell viability slightly decreased with the increase of micelle concentration, but on the whole the cell viability is more than 90%, which is consistent with biocompatibility standard.

Drug Loading Properties of the Reducible Degradable Hyperbranched Polymeric Micelles Taking the reducible degradation of hyperbranched polymer CP21 prepared in Example 1 as an example. The micelle sample CP21 is taken as an example.

(1) Preparation of Drug Loaded Micelles:

Taking 20 mL of the hyperbranched polymeric micelle solution with concentration of 0.5 mg/mL, and 10 mL of methotrexate solution with concentration of 0.1 mg/mL is added under magnetic stirring for 24 hours at the room temperature, then the solution is transferred to a dialysis bag (cutoff molecular weight 3500) for dialyzing 24 hours, the dialysate is changed every 3 hours, and the drug loaded micelle is filtered by 0.45 μm microporous filter membrane. The product obtained is yellowish.

Figure 8:
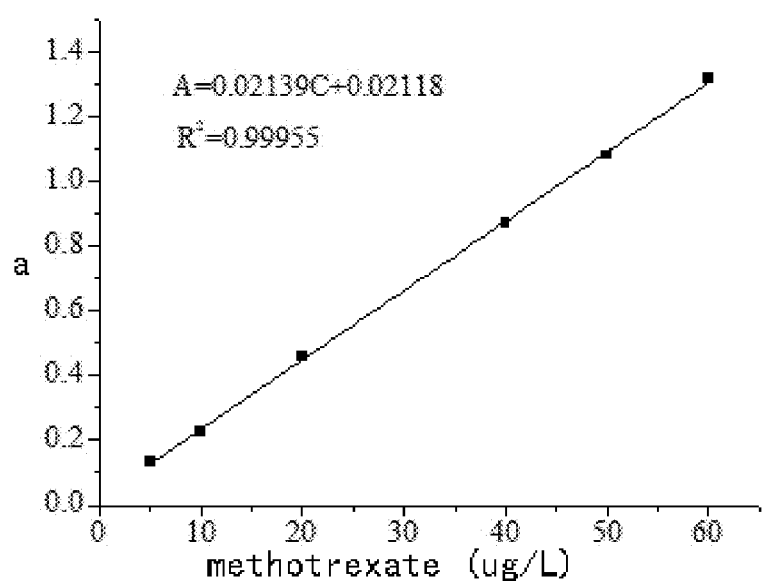
FIG. 8 shows a standard curve of absorbance against methotrexate concentration.

(2) Drug Loading Rate of Hyperbranched Polymer Micelles:

After freeze drying the drug loaded polymer micelles 5.6 mg are dissolved in DMSO with the aid of ultrasound for one hour, then the solution is fixed in a capacity bottle to 10 mL. The absorbance was measured by ultraviolet photometer monitored at 388 nm, and the drug concentration in DMSO is calculated through the standard curve of methotrexate (FIG. 8). The drug loading rate of the polymer micelles is calculated by the following formula:

$$LR(\%) = \frac{W_D}{W_S} \times 100\%$$

Where $W_D$ is the drug weight loaded in the micelles, mg; $W_S$ is the weight of micelles before drug loading, mg;

Based on the calculation the drug loading rate to methotrexate is 10.32wt %. It can be seen that the reducible degradable hyperbranched polymeric micelles shows high drug loading rate due to the three-dimensional cavity structure.

The above description is only a preferred method of implementation of the invention, and is not used to limit the invention. It should be noted that, for ordinary technical personnel in the field of technology, some improvements and variations can be made under the technical principles of the invention. These improvements and variations should also be considered as the scope of protection of the invention.

What is claimed is:

1. A method of preparing reducible degradable hyperbranched polymeric micelles comprising:
   (1) obtaining cystamine by neutralization reaction of cystamine dihydrochloride with a sodium hydroxide solution, which results in a mixture comprising the cystamine, and then extraction of the cystamine from the mixture comprising the cystamine;
   (2) conducting a nucleophilic substitution reaction of the cystamine and polyethylene glycol diglycidyl ether to obtain reducible degradable hyperbranched polymers; and
   (3) dialyzing the reducible degradable hyperbranched polymers to produce the reducible degradable hyperbranched polymeric micelles.

2. The method of claim 1, wherein in step (1): 66.7 mL of 40wt % sodium hydroxide solution and 12.15 g of cystamine dihydrochloride are used, and the reaction is carried out in an ice bath, and the extraction is conducted with a mixture of 50 mL ether and 18 mL tetrahydrofuran.

3. The method of claim 1, wherein in step (2): the polyethylene glycol diglycidyl ether has a molecular weight of 352.

4. The method of claim 1, wherein in step (2): the nucleophilic substitution reaction is conducted in an oil bath at 60° C. for 24 hours.

5. The method of claim 1, wherein in step (2): the nucleophilic substitution reaction is carried out in a solvent of 16 mL deionized water.

6. The method of claim 1, wherein in step (3): the dialyzing is conducted for no less than 48 hours in a dialysis bag with a cutoff molecular weight of 3500.

7. The method of claim 1, wherein in step (2): molar ratio of cystamine to polyethylene glycol diglycidyl ether is set as 3:1, 2:1, 2:2, or 2:3.

* * * * *